United States Patent [19]
D'Aragona et al.

[11] Patent Number: 5,948,361
[45] Date of Patent: Sep. 7, 1999

[54] CHEMICAL SENSOR AND METHOD OF MAKING SAME

[75] Inventors: Frank T. Secco D'Aragona; Henry G. Hughes, both of Scottsdale, Ariz.; Lionel Lescouzeres; Jean-Paul Guillemet, both of Toulouse, France

[73] Assignee: Motorola, Inc., Schaumburg, Ill.

[21] Appl. No.: 08/703,830

[22] Filed: Aug. 27, 1996

[51] Int. Cl.⁶ .................................................. G01N 27/00
[52] U.S. Cl. ............................................................ 422/98
[58] Field of Search ................................................. 422/98

[56] References Cited

U.S. PATENT DOCUMENTS

| | | | |
|---|---|---|---|
| 4,324,761 | 4/1982 | Harris | 422/98 |
| 4,343,768 | 8/1982 | Kimura | 422/98 |
| 4,706,493 | 11/1987 | Chang et al. | 422/98 |
| 4,786,476 | 11/1988 | Munakata et al. | 422/98 |
| 4,892,834 | 1/1990 | Rauh | 422/98 |
| 4,984,446 | 1/1991 | Yagawara et al. | 422/98 |
| 5,012,671 | 5/1991 | Yagawara et al. | 422/98 |
| 5,250,170 | 10/1993 | Yagawara et al. | 422/98 |

*Primary Examiner*—Timothy Speer
*Attorney, Agent, or Firm*—Daniel R. Collopy; Rennie W. Dover

[57] ABSTRACT

A chemical sensor (10) is formed in part by depositing a stack of dielectric and resistive layers (13–15) on a support substrate (11). A cavity (17) is then formed on a substrate (16) to provide thermal isolation to the chemical sensor (10). The stack of dielectric and resistive layers (13–15) is then bonded to the substrate (16) and the support substrate (11) is removed. A layer of chemical sensing material (30) is then formed on the uppermost dielectric layer (15). Openings (33) may be formed through the stack of dielectric and resistive layers (13–15) to further enhance the thermal isolation of the chemical sensor (10) from the substrate (16).

10 Claims, 1 Drawing Sheet

CHEMICAL SENSOR AND METHOD OF MAKING SAME

BACKGROUND OF THE INVENTION

This invention relates, in general, to electronic components and, more particularly, to chemical sensing devices and methods of making the same.

Chemical sensing devices are used in applications where it is necessary to detect the presence of a gas in an ambient and indicate the presence of the gas to an integrated circuit. For example, a carbon monoxide detector comprises a sensor that enables an integrated circuit to sound an alarm when the sensor detects the presence of carbon monoxide.

Such chemical sensors are typically formed by micromachining a silicon substrate and forming a sensing element on the silicon substrate. The sensing element consists of a layer of chemical sensing material, such as tin oxide, that is formed on a heating element. The heating element is used to heat the layer chemical sensing material to approximately 350 degrees centigrade (°C.). At the elevated temperature, the resistivity of the layer of chemical sensing material changes due to the presence of the gas to be detected. For example, the resistivity of tin oxide changes significantly when heated to 350° C. and placed in the presence of carbon monoxide. The change in resistivity can be measured and be used to indicate the presence of carbon monoxide.

Thus, the layer of chemical sensing material must be heated to a high temperature and that temperature must be maintained during operation. Due to the conductive nature of the materials commonly used to form chemical sensors (e.g., silicon substrates), there is a significant loss of thermal energy as the chemical sensor is operated. To reduce this thermal loss, and thus the amount of energy that is consumed by a chemical sensor, the heating element and chemical sensing material are formed on a thin membrane that is connected to a silicon substrate. The process used to form the thin membrane includes an anisotropic etch to remove the bulk of the silicon substrate under the heating element.

The process of forming the thin membrane introduces several problems when the chemical sensors are formed in a high volume production operation. First, it is difficult to control the etch rate of the anisotropic etch so the final thickness and uniformity of the thin membrane will vary from one manufacturing lot to the next and even across a wafer in a manufacturing lot. If the membrane is thinned too much, the anisotropic etch can damage the heating element and the layer of chemical sensing material. Another problem associated with this process is that it is necessary to align the anisotropic etch process, which occurs on the backside of the silicon substrate, to the process used to form the heating element and chemical sensing material on the front side of the silicon substrate. Backside alignment techniques not only complicate the manufacturing process, but add significant cost to the chemical sensor.

By now it should be appreciated that it would be advantageous to provide a method of making a chemical sensor that did not require the formation of a thin membrane to provide thermal isolation. It would also be advantageous if the method did not require the use of backside alignment techniques as part of the manufacturing process used to form the chemical sensor.

Figure 1:
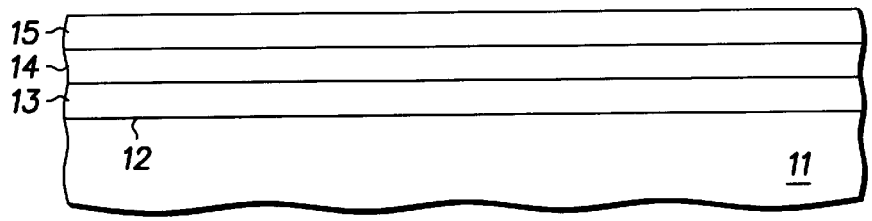
FIGS. 1–4 are enlarged cross-sectional views of a chemical sensor at various points in a manufacturing process used to form the chemical sensor in accordance with the present invention.

It will be appreciated that for simplicity and clarity of illustration, elements illustrated in the figures have not necessarily been drawn to scale. For example, the dimensions of some of the elements are exaggerated relative to other elements for clarity. Further, where considered appropriate, reference numerals have been repeated among the figures to indicate corresponding or analogous elements.

DETAILED DESCRIPTION OF THE DRAWINGS

FIG. 1 is an enlarged cross-sectional view of a portion of a chemical sensor 10 at an early stage in the fabrication process in accordance with the present invention. The portion of chemical sensor 10 shown in FIG. 1 is formed on a support substrate 11, which is preferably a silicon substrate. The formation of chemical sensor 10 begins by forming a dielectric layer 13 on a surface 12 of support substrate 11. Dielectric layer 13 is preferably a layer of silicon dioxide that is about 300 angstroms to 30,000 angstroms thick and can be formed using one of three processes: a chemical vapor deposition (CVD) process, a plasma enhanced chemical vapor deposition (PECVD) process, or a thermal oxidation process of substrate 11. As will be explained below, dielectric layer 13 is used as an etch stop layer and thus could be formed from other materials that have similar characteristics such as silicon nitride, or the like.

A layer of resistive material 14 is then formed on dielectric layer 13, which is used to form a heating element of chemical sensor 10. A variety of materials can be used to form layer of resistive material 14 including polysilicon, amorphous silicon, and metals having poor conductivity. Preferably, layer of resistive material 14 is about 300 angstroms to 30,000 angstroms thick and has a resistivity such that when a current is passed through layer of resistive material 14, enough heat is generated to elevate layer of sensing material 30 to the proper operational temperature. For example, layer of resistive material 14 can have a resistance range of about $1 \times 10^{-6}$ ohm-centimeter (cm) to $1 \times 10^{-3}$ ohm-cm. A conventional CVD or PECVD process can be used to deposit a layer of polysilicon or amorphous silicon in order to form layer of resistive material 14 having the desired resistivity.

To complete the structure shown in FIG. 1, a second dielectric layer 15 is formed on layer of resistive material 14. Preferably, dielectric layer 15 is a layer of silicon dioxide that is deposited using a PECVD process. For example, the PECVD process uses tetraethylorthosilicate (TEOS) in a plasma reaction chamber. Other processes such as a CVD deposition of silicon dioxide or the thermal oxidation of layer of resistive material 14 could be used to form dielectric layer 15. A PECVD process is preferred because the properties of the silicon dioxide layer are optimized for a wafer bonding process to follow. In particular, the planarity of a silicon dioxide layer (dielectric layer 15) is well suited for bonding to flat surfaces. The preference of forming dielectric layer 15 from a PECVD process is not considered a limitation of the present invention. Dielectric layer 15 has a preferred thickness of about 300 angstroms to 30,000 angstroms and can be formed from other dielectric materials such as silicon nitride or the like.

Figure 2:
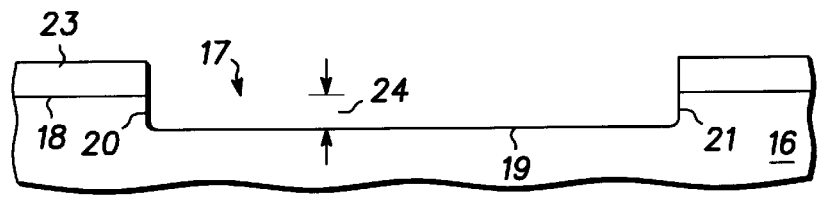

FIG. 2 is an enlarged cross-sectional view of a substrate 16, which is used to provide a portion of chemical sensor 10. Preferably, substrate 16 is a silicon substrate and has a thickness 26 of at least 300 microns. The thickness of substrate 16 provides more structural support and is more tolerant of physical stress than the thin membrane that is used to support previously known chemical sensors. Thermal isolation is provided for chemical sensor 10 by forming a cavity 17 in substrate 16. This is in contrast to forming a thin membrane out of substrate 16.

Cavity 17 is formed by depositing and patterning an etch layer 23 on a surface 18 of substrate 16. Etch layer 23 can be a layer of photoresist that is formed using conventional photolithographic techniques. A reactive ion etch (RIE) etch is then used to remove the exposed portions of substrate 16. When an RIE etch is used, cavity 17 has a first side 20 and a second side 21 that extend from surface 18 such that there are substantially perpendicular with surface 18. Cavity 17 also has a bottom side 19 positioned between sides 20 and 21 and it is essentially parallel with surface 18 of substrate 16. The perpendicular and parallel portions of cavity 17 are a result of the RIE etch process used to form cavity 17. It is not necessary that sides 20 and 21 be exactly perpendicular or that bottom surface 19 be exactly parallel because normal process variations are more than acceptable. As will be explained in more detail below, cavity 17 is used to provide thermal isolation to the portion of chemical sensor 10 that is formed above cavity 17. The effectiveness of the thermal isolation is predominantly determined by the depth of cavity 17 and is not affected by variations in the geometries of sides 20 and 21 and bottom side 19.

Cavity 17 could also be formed using an anisotropic etch process. A wet etch solution comprising potassium hydroxide (KOH), tetramethylammoniumhydroxide (TMAH), or the like is used to remove the exposed portion of substrate 16. These wet etch solutions perform an anisotropic etch and form cavity 17 such that the sides 20 and 21 of cavity 17 are sloped instead of being perpendicular. As is understood in the art, these wet etch solutions etch preferably silicon along crystal faces and form sides that are at an angle of 54.7 degrees. Cavity 17 is formed with a depth 24 of about 1 micron to 75 microns. Depth 24 is determined as the distance between bottom surface 19 and surface 18 extended above bottom surface 19.

One advantage of the present invention is that it is relatively easy to control depth 24 by controlling the relative etch time of the RIE etch or the anisotropic etch process. It is not necessary to rely on a doped region or an etch barrier to control the anisotropic etch process as is commonly done in the art. Another advantage of the present invention is that depth 24 is relatively small compared to the thickness 26 of substrate 16. Therefore, the presence of cavity 17 does not significantly affect the structural integrity of substrate 16. After cavity 17 is formed, etch layer 23 is removed to allow further processing.

Figure 3:
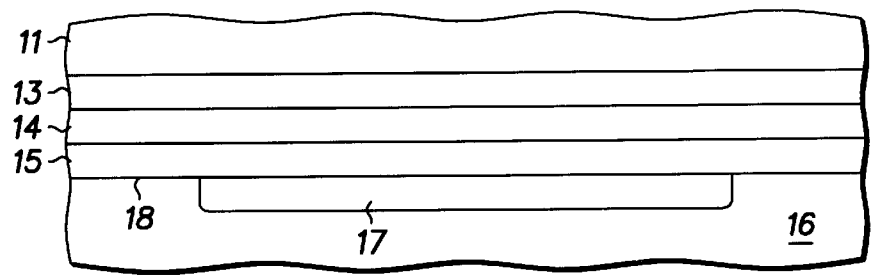

Referring now to FIG. 3, dielectric layer 15 is bonded to surface 18 of substrate 16. A conventional bonding process can be used where dielectric layer 15 is placed in physical contact with substrate 16 and then heated to about 1000° C. to 1200° C. for about 1 hour to two hours. After bonding, support substrate 11 is removed with a grinding process, a polishing process, a wet etch solution or a combination of the three. In the preferred embodiment, support substrate 11 is removed with a grinding process and dielectric layer 13 is used as an etch stop utilizing a wet etch anisotropic process.

Figure 4:
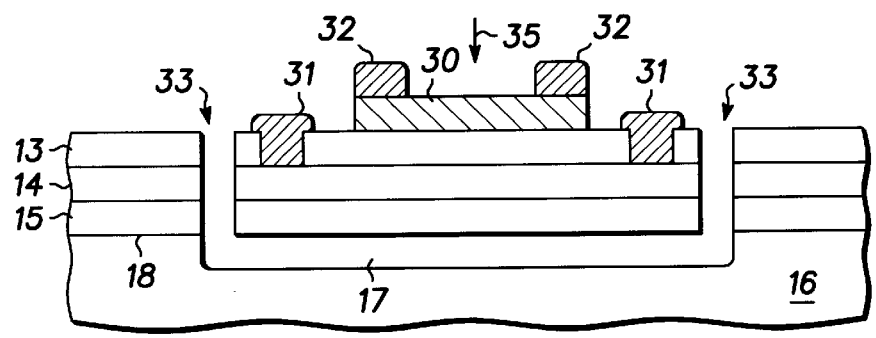

Turning now to FIG. 4, the method of making chemical sensor 10 continues by forming a layer of chemical sensing material 30 on dielectric layer 13. Layer 30 is preferably about 300 angstroms to 30,000 angstroms thick and comprises materials such as tin, tin oxide, palladium, palladium oxide, tungsten oxide, or other metal oxides. Layer 30 can also be made from polymeric sensing materials such as phthalocyanines. The choice of material used to form layer 30 will depend on the chemical that is to be detected in an ambient 35 above layer 30. For example, tin oxide is used to form layer 30 when the presence of carbon monoxide is to be detected in ambient 35. The process used to form layer 30 will depend on the composition of the material used and, in general, can be formed with a sputtering process, an evaporation process, or a CVD process. The material is then patterned to provide layer 30 shown in FIG. 4.

Then the necessary electrical contacts are made to layer of chemical sensing material 30 and layer of resistive material 14. Conventional metallization techniques known in the art are used to form contacts 31 and 32, which are electrically connected to layer 14 and layer 30, respectively. To operate chemical sensor 10, an electrical current is passed between contacts 31 via layer of resistive material 14. As a result, layer of resistive material 14 will heat layer of chemical sensing material 30 to the proper temperature. Contacts 32 are used to monitor the resistivity of layer 30. When the proper chemical enters ambient 35, the resistivity of layer 30 will change to indicates the presence of the chemical in a gas or fluid. External circuitry (not shown) is used to monitor the change in resistivity and report this information as necessary to indicate the presence of the chemical.

Optionally, the method of making chemical sensor 10 can include the formation of openings 33. Openings 33 can be formed with an RIE or wet etch process that removes the desired portions of dielectric layer 13, layer of resistive material 14, and dielectric layer 15. Preferably, openings 33 are formed above cavity 17 to further enhance the thermal isolation of chemical sensor 10. Opening 33 provide thermal isolation by physically separating chemical sensor 10 from neighboring structures and thus the size of openings 33 depends on the amount of thermal isolation needed. Openings 33 also relieve any pressure that may have built in cavity 17 during the formation of chemical sensor 10 or that may arise due to the elevated operating temperatures of chemical sensor 10. The cross-section taken to provide FIG. 4 passes through openings 33 for clarity. It should be understood that chemical sensor 10 is suspended above cavity 17 by the portions of dielectric layer 15 that extend into and out of the cross-section shown in FIG. 4.

Figure 5:
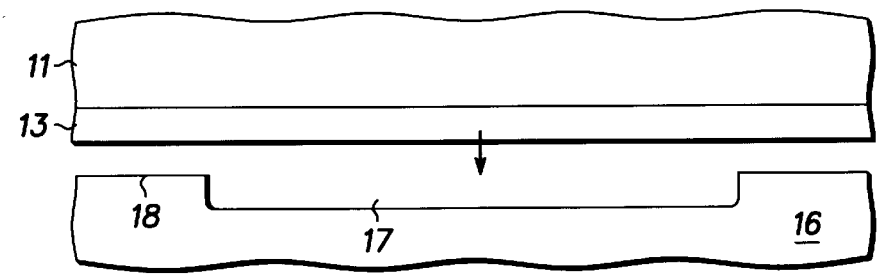
FIG. 5 is an enlarged cross-sectional view of the chemical sensor formed by an alternative method in accordance with the present invention.

FIG. 5 is provided to illustrate an alternative method of forming chemical sensor 10. As described earlier, support substrate 11 is used to support layers 13, 14, and 15. It not necessary that layers 13–15 be formed on support substrate 11, as it is considered equivalent to form some of these layers 13–15 on support substrate 11, transfer them to substrate 11, and form the remaining layers 14–15 on substrate 16. As shown in FIG. 5, only dielectric layer 13 is formed on support substrate 11. Dielectric layer 13 is then bonded to surface 18 of substrate 16. After removing support substrate 11 with one of the techniques described above, layer of resistive material 14, dielectric layer 15, and layer of chemical sensing material 30 (see FIG. 4) are formed over dielectric layer 13.

By now it should be appreciated that the present invention provides a novel chemical sensor and a method of making the same. One advantage of the present invention is that the delicate portions of chemical sensor 10 (e.g., layer of resistive material 14) are not exposed to a harsh etch solution. In the present invention, only substrate 16 is exposed to the anisotropic etch process so there is no risk of damaging layer of resistive material 14 or layer of chemical sensing material 30 during the formation of cavity 17. In addition, the process used to form cavity 17 does not require the use of a backside alignment process. Backside alignment processes are commonly used in the art to align the formation of the thin membrane so that it is under the chemical sensor. The present invention obviates the need to use a backside alignment process, therefore the method of forming chemical sensor 10 is simpler and less expensive.

In the examples provided hereinbefore, both support substrate 11 and substrate 16 are silicon substrates. This is preferred because of the familiarity of these substrate in high volume manufacturing. It should be understood that this is not a limitation of the present invention as support substrate 11 and substrate 16 could also be a ceramic substrate, a glass substrate, a compound semiconductor substrate, or the like. These substrates 11 and 16 could also be formed from a dielectric material such as silicon dioxide or silicon nitride.

In the preferred embodiment, a PECVD process was used to form dielectric layer 15. This is because the PECVD process provides a film that is optimal for bonding to substrate 16. It should be understood that it may be necessary to lightly polish dielectric layer 15 prior to bonding to form a planar surface. If underlying topography or the deposition process used to form dielectric layer 15 results in a rough surface, the light polishing will improve the planarity of dielectric layer 15.

We claim:

1. A chemical sensor comprising:
   a substrate having a surface and a cavity, wherein the cavity comprises a first side, a second side, and a bottom side, the first side and the second side extend from the surface into the substrate and the bottom side is positioned between the first side and the second side and is substantially parallel with the surface of the substrate;
   a first layer of dielectric material overlying the cavity of the substrate, wherein the first layer of dielectric material is bonded to the surface of the substrate;
   a layer of resistive material overlying the first layer of dielectric material;
   a second layer of dielectric material overlying the layer of resistive material; and
   a layer of chemical sensing material overlying the second layer of dielectric material.

2. The chemical sensor of claim 1 further comprising an opening passing through the second layer of dielectric material, the layer of resistive material, and the first layer of dielectric material, wherein the opening is overlying the cavity of the substrate.

3. The chemical sensor of claim 1 wherein the first layer of dielectric material is a layer of plasma enhanced chemical vapor deposition silicon dioxide.

4. The chemical sensor of claim 1 wherein the layer of resistive material has a resistivity of about $1 \times 10^{-6}$ ohm-cm to $1 \times 10^{-3}$ ohm-cm.

5. The chemical sensor of claim 1 wherein the layer of chemical sensing material comprises a material selected from the group consisting of tin, tin oxide, palladium, phthalocyanines, tungsten oxide, and palladium oxide.

6. The chemical sensor of claim 1 wherein the substrate is at least 300 microns thick.

7. The chemical sensor of claim 1 wherein the cavity has a depth defined from the surface of the substrate to the bottom side, which is about 1 micron to 75 microns.

8. The chemical sensor of claim 1 wherein the first side and the second side of the cavity extend from the surface of the substrate such that the first side and the second side are substantially perpendicular to the surface of the substrate.

9. A sensor comprising:
   a substrate having a surface and a cavity, wherein the cavity comprises a first side, a second side, and a bottom side, the first side and the second side extending from the surface into the substrate, and the bottom side being positioned between the first side and the second side and being substantially parallel with the surface of the substrate;
   a first layer of dielectric material overlying the cavity of the substrate, wherein the first layer of dielectric material is bonded to the surface of the substrate to provide a bonding interface between the first layer of dielectric material and the substrate;
   a layer of resistive material overlying the first layer of dielectric material, wherein the cavity provides thermal isolation between heat generated in the layer of resistive material and the substrate;
   a second layer of dielectric material overlying the layer of resistive material;
   a layer of chemical sensing material overlying the second layer of dielectric material; and
   wherein the sensor has an opening overlying the cavity of the substrate and passing through the second layer of dielectric material, the layer of resistive material, and the first layer of dielectric material.

10. A sensor comprising:
    a substrate having a surface and a cavity, wherein the cavity comprises a first side, a second side, and a bottom side, the first side and the second side extending from the surface into the substrate, and the bottom side being positioned between the first side and the second side and being substantially parallel with the surface of the substrate;
    a first layer of dielectric material overlying the cavity of the substrate;
    a layer of resistive material overlying the first layer of dielectric material;
    a second layer of dielectric material overlying the layer of resistive material;
    a layer of chemical sensing material overlying the second layer of dielectric material; and
    wherein the sensor has an opening passing through the second layer of dielectric material, the layer of resistive material, and the first layer of dielectric material.

* * * * *